US006078671A

United States Patent [19]

Kawanishi et al.

[11] Patent Number: 6,078,671

[45] Date of Patent: Jun. 20, 2000

[54] SILENCER FOR ATTENUATING A SOUND OR NOISE TRANSMITTED THROUGH AN AIR PASSAGE OF A DUCT

[75] Inventors: Takashi Kawanishi; Masayoshi Ikeda, both of Kanagawa-ken, Japan

[73] Assignee: Ebara Corporation, Tokyo, Japan

[21] Appl. No.: 08/923,397

[22] Filed: Sep. 4, 1997

[30] Foreign Application Priority Data

Sep. 5, 1996 [JP] Japan .................................... 8-257437
Sep. 5, 1996 [JP] Japan .................................... 8-257438

[51] Int. Cl.[7] ............................ A61F 11/06; H03B 29/00

[52] U.S. Cl. .......................................... 381/71.5; 381/71.1

[58] Field of Search ................................ 381/94.1, 71.1, 381/71.5, 368, 359

[56] References Cited

U.S. PATENT DOCUMENTS

| | | | |
|---|---|---|---|
| 4,191,096 | 3/1980 | Ramsey | 381/368 |
| 4,514,598 | 4/1985 | Plice | 381/368 |
| 4,991,220 | 2/1991 | Wolf | 381/368 |
| 5,031,872 | 7/1991 | Vance | 381/368 |
| 5,606,622 | 2/1997 | Christenson | 381/71.5 |

FOREIGN PATENT DOCUMENTS

| | | |
|---|---|---|
| 5-223333 | 8/1993 | Japan . |
| 5-223335 | 8/1993 | Japan . |
| 6-117399 | 4/1994 | Japan . |

*Primary Examiner*—Minsun Oh Harvey
*Attorney, Agent, or Firm*—Oblon, Spivak, McClelland, Maier & Neustadt, P.C.

[57] ABSTRACT

A silencer is adapted to be mounted on an air duct. The silencer includes a noise detecting microphone for detecting a noise transmitted through the air passage of the duct, a loud speaker for delivering on the basis of the noise detected by the microphone into the air passage a sound which is substantially the same as the noise except that the phase of the sound is the reverse of that of the noise to thereby enable the sound to be superimposed on the noise and attenuate the noise, and vibration shield provided between the microphone and the wall of said duct for shielding any vibrations transmitted through the wall to the microphone. The vibration shield includes a duct element made from a sound absorbing material which element forms a part of the duct and the noise detecting microphone is mounted to the duct element. Alternatively, the vibration shield can include a vibration shield member mounted on the outside of the duct where an opening is provided in the wall of the duct and a noise detecting microphone is provided with a windscreen around a sound collecting portion of the microphone. The windscreen is inserted into a through hole provided in the shield member to fasten the microphone.

20 Claims, 5 Drawing Sheets

SILENCER FOR ATTENUATING A SOUND OR NOISE TRANSMITTED THROUGH AN AIR PASSAGE OF A DUCT

BACKGROUND OF THE INVENTION

1. Field of the Invention

This invention relates to a silencer mounted on an air duct for attenuating a noise transmitted through the air passage of the duct.

2. Discussion of the Background

FIG. 7 shows a prior art silencer 200 mounted on an air duct 202 only a part of which is shown and which is usually made from steel. The duct has a blower 204 for generating an air flow passing through the air passage thereof. The silencer includes a noise detecting microphone 208 provided on the duct wall and covering a through hole 210 formed in the duct wall to detect a noise generated by the blower and transmitted through the air passage, a loud speaker 212 provided on the duct wall at a position spaced away from the microphone 208 and covering a through hole 214 formed in the duct wall for delivering a sound which is substantially the same as the noise stated above except that the phase of the sound is the reverse of that of the noise to thereby enable the sound to be superimposed on the noise transmitted through the air passage of the duct so as to attenuate the noise, and, a control 216 for receiving an electrical signal representing the noise from the microphone 208 and generating and delivering an electrical signal representing the sound referred to above to the loud speaker.

FIG. 8 shows another prior art silencer 220 which is substantially the same as that shown in FIG. 7 except that the noise detecting microphone 208 is provided on a strut 222 extending from the inner surface of the duct wall radially inwardly.

FIGS. 9 and 10 show a silencer 224 in accordance with an earlier technology which is substantially the same as that shown in FIG. 7, but which includes a plurality of rectangular blades or partitions 226 and an error detecting microphone 228. The blades are made from a sound absorption material and extend radially from the center axis of the air passage of the duct to the inner surface of the duct wall to divide the air passage into seven passage segments extending in parallel with the center axis. An error detecting microphone detects any noise still remaining after the noise attenuation by the superimposition of the sound on the noise as stated above and delivers an error signal to the control. In this silencer, in addition to attenuation of the noise by superimposition of the sound on the noise as stated in connection with the first prior art, the noise is attenuated by noise absorption by the blades.

However, such silencers involve problems in that the noise source or blower 204 generates vibrations which are transmitted through the duct wall to the microphone 208. Further, vibrations caused by the loud speaker 212 are also transmitted to the noise detecting microphone 208. Accordingly, the noise detecting microphone detects those vibrations and, thus, it is impossible for the microphone to appropriately detect the noise transmitted through the air passage of the duct. This means that it is impossible for the prior art silencers to appropriately and adequately attenuate noise.

SUMMARY OF THE INVENTION

It is therefore an object of this invention to provide a silencer in which a noise detecting microphone can detect noise transmitted through the air passage of a duct by shielding any vibrations transmitted through the duct wall as much as possible.

In accordance with this invention, there is provided a silencer including a noise detecting microphone mounted on a duct for detecting a noise transmitted through the air passage of the duct, a loud speaker mounted on the duct to deliver on the basis of the noise detected by the microphone into the air passage a sound which is substantially the same as said noise except that the phase of the sound is the reverse of that of the noise to thereby enable the sound to be superimposed on the noise to thereby attenuate the noise, and vibration shield means provided between the microphone and the wall of the duct for shielding any vibrations transmitted through the wall to the microphone so that the microphone detects the noise without any noise interference caused by the vibrations.

In a preferred embodiment, the vibration shield means includes a duct element made from a vibration damping or sound absorbing material such as glass wool and adapted to be incorporated into the duct to form a part of the same and the noise detecting microphone is mounted on the duct element.

The duct element can include a duct element body made from a vibration damping or sound absorbing material and a rigid solid cover provided over the radially outer surface of the duct element body. The cover provides rigidity to the duct element and further shields a sound to be transmitted from the air passage of the duct to the atmosphere through the duct element. In such a case, the duct element body is provided with a through hole radially extending therethrough and the rigid solid cover is provided with an opening aligned with the through hole of the duct element body and having a diameter larger than that of the through hole. The microphone is provided with a windscreen made from an open cell type porous elastomer provided around the noise or sound collecting portion of the microphone and the windscreen is securely inserted into the through hole of the duct element body to thereby mount the microphone on the duct element.

The windscreen inserted into the through hole of the duct element body can have a radially inner surface which is substantially flush with the inner surface of the duct element body and a radially outer surface provided with a recess therein. The microphone is mounted on the radially outer surface of the windscreen in such a manner that the noise or sound collecting portion is inserted into the recess without any contact with the inner surface of the recess.

The microphone can have a fastening member connected thereto and securely inserted into the recess to thereby fasten the microphone on the windscreen. A cushion member may be provided between and engaged with the radially outer surface of the windscreen and the microphone fastened on the windscreen. The cushion member adds mass to the vibration system including the microphone and the windscreen, whereby the microphone is made less sensitive to high frequency vibrations transmitted to the microphone through the windscreen.

The duct element can further include a sound permeable liner provided over the radially inner surface of the duct element body. The liner prevents any fractions of the material of the duct element body or vibration damping or sound absorbing material from falling into the air passage.

The silencer can further include a solid cup-like cover member covering the radially outer surface of the windscreen and the microphone mounted on the radially outer surface of the windscreen with a space left therebetween and sealingly connected to the outer surface of the rigid solid cover provided over the duct element body outside of the opening provided in the cover.

The silencer can further include an error detecting microphone for detecting any noise still remaining after the noise attenuation by the superimposition of the sound on the noise stated above. The noise detecting microphone, the loud speaker and the error detecting microphone are mounted on the duct element downstream of a source of the noise in the noise transmission direction in that order and spaced away from each other.

The silencer can further include partition walls provided in the duct element in such a manner that the walls radially extend from the central axis of the air passage of the duct element to the inner wall of the duct element to divide the air passage into a plurality of air passage segments extending in parallel with the center axis, the partition walls being made from a vibration damping or sound absorption material.

In a further embodiment, a silencer includes a noise detecting microphone mounted on a duct for detecting a noise transmitted through the air passage of the duct, a loud speaker mounted to the duct to deliver on the basis of the noise detected by the microphone into the air passage a sound which is substantially the same as said noise except that the phase of the sound is the reverse of that of the noise to thereby enable the sound to be superimposed on the noise to thereby attenuate the noise, and, a vibration shield member made from a vibration damping or sound absorption material mounted on the outside of the duct where an opening is provided in the wall of the duct. The vibration shield member has a through hole extending radially relative to the duct and a windscreen made from an open cell type porous elastomer installed into the through hole. The windscreen has a recess formed in the radially outer surface of the windscreen and the noise detecting microphone is mounted on the radially outer surface of the windscreen in such a manner that the noise collecting portion of the microphone is positioned in the recess without any contact with the inner surface of the recess. The radially inner surfaces of the windscreen and the vibration shield member are substantially flush with the inner surface of the duct. The microphone has a fastening member connected thereto and securely inserted into the recess of the windscreen to thereby fasten the microphone on the windscreen.

A cushion member is provided between and engaged with the radially outer surface of the windscreen and the noise detecting microphone to add mass to the vibration system including the microphone and the windscreen, whereby the microphone is less sensitive to high frequency vibration transmitted to the microphone through the windscreen.

The silencer can further include a first cover member covering the outer surface of the vibration shield member and sealingly connected to the outer surface of the duct. The cover member has an opening whereby the radially outer surface of the windscreen provided in the through hole of the noise shield member is exposed and the cover member does not engage with any portion of the radially outer surface of the windscreen. A second cover member can be sealingly connected to the radially outer surface of the first cover member outside of the opening noted above and covering the microphone on the windscreen without any contact with the same.

These and other objects of this invention will become clear from the following detailed description of preferred embodiments when taken in conjunction with the accompanying drawings.

DESCRIPTION OF THE PREFERRED EMBODIMENT

Figure 1:
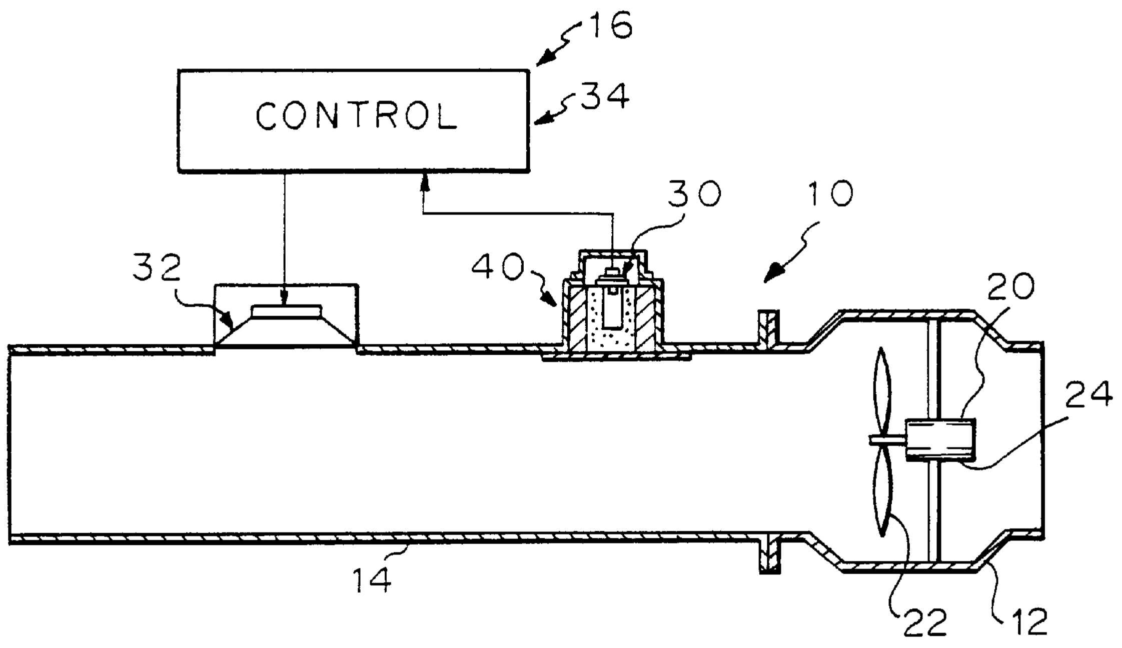
FIG. 1 is a cross-sectional view of a duct provided with a silencer in accordance with the first embodiment of this invention.
Figure 2:
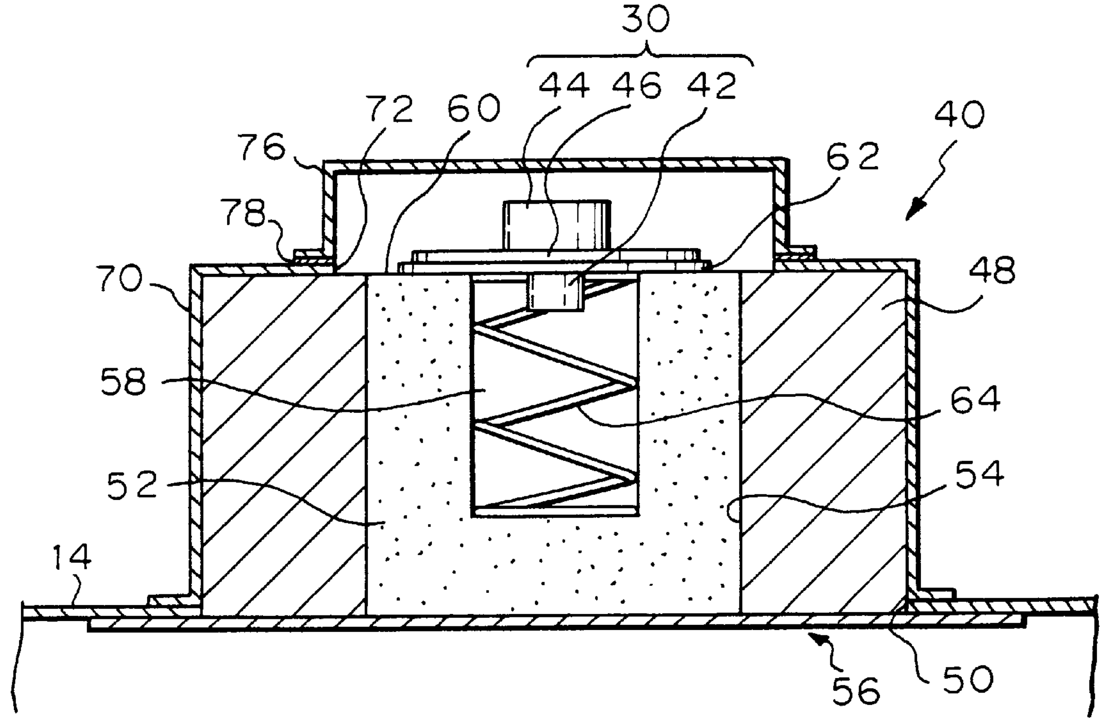
FIG. 2 is an enlarged cross-sectional view of a noise detecting microphone and a microphone mounting device in the silencer shown in FIG. 1.

Referring now to FIGS. 1 and 2, there is shown part of a steel duct 10 including first and second duct elements 12 and 14 to which part a silencer 16 in accordance with a first embodiment of this invention is mounted. Practically, the duct includes further duct elements (not shown) connected to the opposite ends of the part of the duct shown in FIG. 1.

The first duct element is provided with a blower 20 therein. The blower includes rotary blades 22 and a motor 24 for rotating the rotary blades to generate an air flow passing through the duct in the rightward direction as viewed in FIG. 1.

The silencer 16 includes a noise detecting microphone 30 for detecting a noise induced by the blower 20 and transmitted through the air passage of the duct in the leftward direction and a loud speaker 32 for delivering into the air passage a sound which is substantially the same as the noise detected by the microphone 30 except that the phase of the sound is the reverse of that of the noise in such a manner that the sound is superimposed on the noise to thereby attenuate the same. Reference numeral 34 designates a control for receiving from the microphone 30 an electrical signal representing a noise detected by the microphone 30 and generating and delivering to the loud speaker 32 an electrical signal representing the above-noted sound.

FIG. 2 shows a device 40 for mounting the microphone 30 to the duct, the microphone 30 including a noise or sound collecting portion 42, an amplifier 44 for generating a signal representing a noise detected by the noise collecting portion and delivering the signal to the control 34 and an annular mounting plate 46 provided between the noise collecting portion 42 and the amplifier 44.

The mounting device 40 includes a cylindrical vibration shield member 48 made from a vibration damping or sound absorption material such as glass wool mounted on the outside of the duct where an opening 50 is provided in the wall thereof and a windscreen 52 made from open cell type porous elastomer installed into the through hole 54 of the cylindrical vibration shield member. The vibration shield member 48 and the windscreen 52 are of the same height and the radially inner surfaces thereof are substantially flush with the inner surface of the wall of the duct. A sound permeable web 56 is attached over the opening 50 in the duct wall to prevent fractions of the material of the vibration shield member 48 falling into the air passage of the duct. The windscreen 52 includes a recess 58 provided in the radially outer surface 60 thereof to receive the sound collecting or noise receiving portion 42 of the noise detecting microphone 30 mounted on the outer surface 60 of the same. In this embodiment, an annular cushion member 62 is adhered to the outer surface 60 of the windscreen 52 and the mounting plate 46 is engaged with the outer surface of the annular cushion member in such a manner that the noise collecting portion 42 passes through the center hole of the annular cushion member 62. A coil 64 or fastener means is secured to the mount plate 48 and passes through the center hole of the cushion member 62 to be interference-fitted into the recess 58 of the windscreen 52 so as to fasten the mounting plate 46 on the cushion member 62. The mounting plate 62 provides an additional mass to the vibration system of the mounting device to thereby make the microphone less sensitive to a relatively high frequency zone of the vibration transmitted to the microphone through the windscreen.

In production, the vibration shield member 48 and the windscreen 52 are installed in a steel cover member 70 in the shape of an inverted cup and the cover member with the shield member 48 and the windscreen 52 is welded on the outer surface of the duct along the edge of the opening 50 in such a manner that the vibration shield member 48 and the windscreen 52 are arranged as stated above relative to the opening 50 of the duct. The cover member 70 has an opening 72 at the top wall the diameter of which is larger than that of the through hole 54 of the windscreen so that the cover member 70 does not directly engage with the windscreen 52 to prevent any vibration from being transmitted directly to the windscreen through the duct wall and the cover member.

An additional cover 76 in the shape of an inverted cup is provided on the outer surface of the top wall of the cover member 70 along the periphery of the opening 72 of the cover member 70 covering the amplifier 44 of the microphone 30 with an annular packing member 78 imposed between the cover member 70 and the peripheral flange 80 of the additional cover 76. The opening 50 in the duct wall is therefore sealed from the atmosphere, whereby air leakage from the air passage in the duct to the atmosphere which would occur due to a pressure difference therebetween without the provision of the cover members is prevented.

Figure 3:
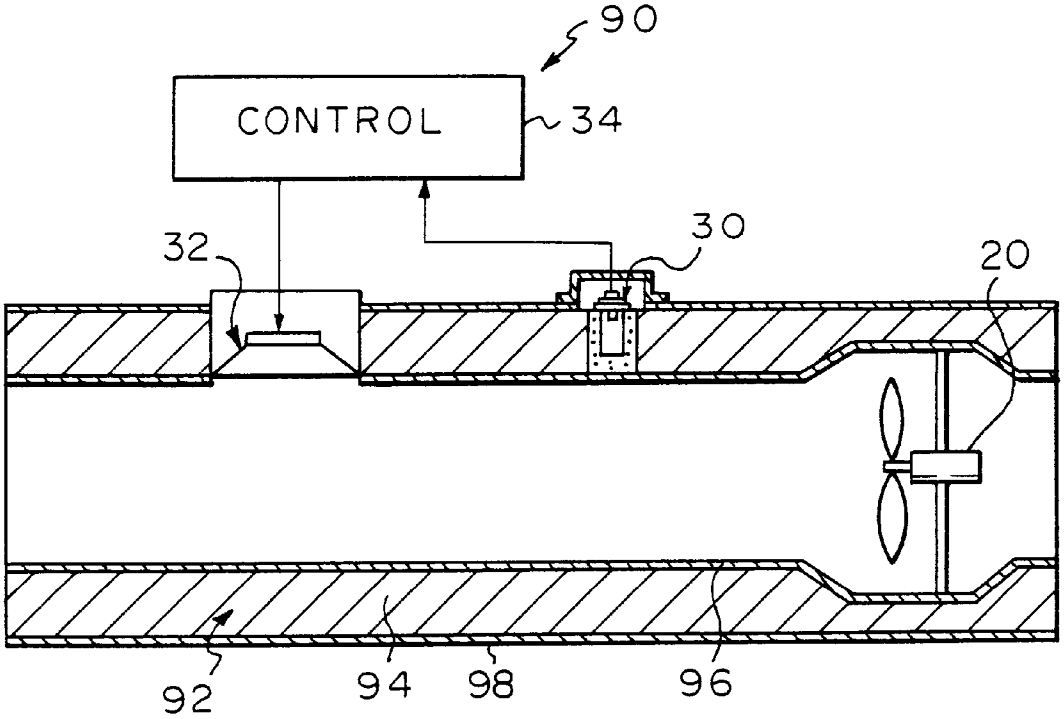
FIG. 3 is a cross-sectional view of a duct provided with a silencer in accordance with the second embodiment of this invention.
Figure 4:
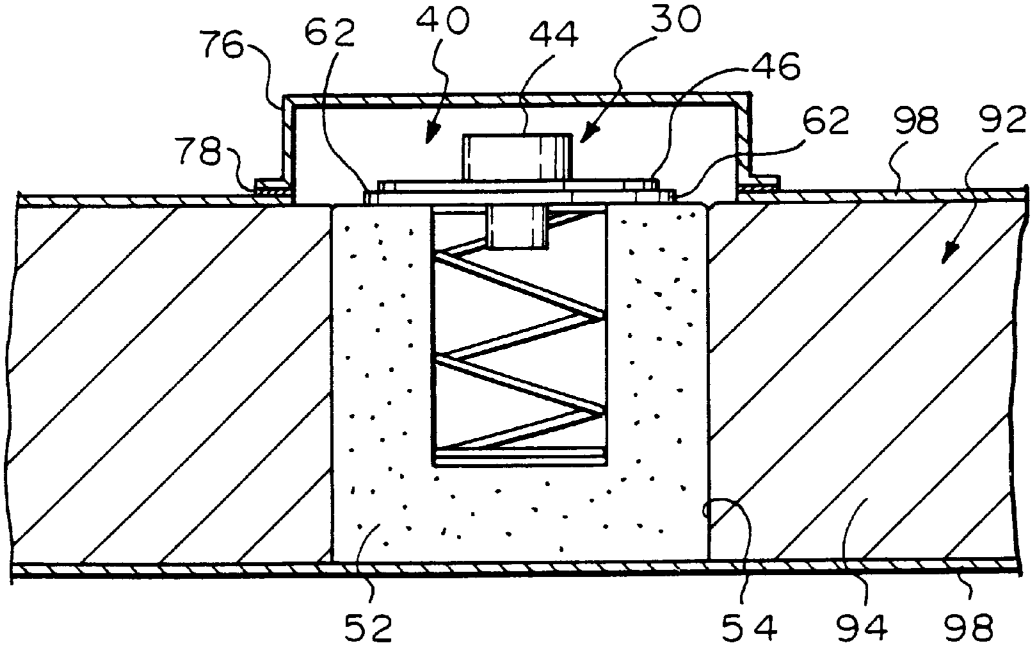
FIG. 4 is an enlarged cross-sectional view of a noise detecting microphone and a microphone mounting device in the silencer shown in FIG. 3.

FIGS. 3 and 4 show a silencer 90 in accordance with a second embodiment of this invention. As shown, the silencer 90 is generally the same as that of the first embodiment except that the duct wall or duct element 92 of the former is per se generally made from a vibration damping or sound absorption material such as glass wool and thus a microphone mounting device is somewhat modified accordingly. Thus, the elements of the silencer which are the same as those of the first embodiment are designated by the same reference numbers. The duct element 92 includes a wall body or duct element body 94 made from glass wool, a sound permeable web or liner 96 laid over the inner surface of the wall body 94 and a steel sheet cover 98 laid over the outer surface of the wall body. The duct element 92 comprises a combination of the first and second duct elements in the first embodiment integrally formed with each other and is provided with a blower 20 at the right end thereof.

The silencer includes a microphone 30, a loud speaker 32 and a control 34 which are substantially the same as those of the first embodiment. As best shown in FIG. 4, the microphone mounting device 40 is the same as that of the first embodiment except that it does not include a member corresponding to the cover member 70 of the first embodiment.

Figure 5:
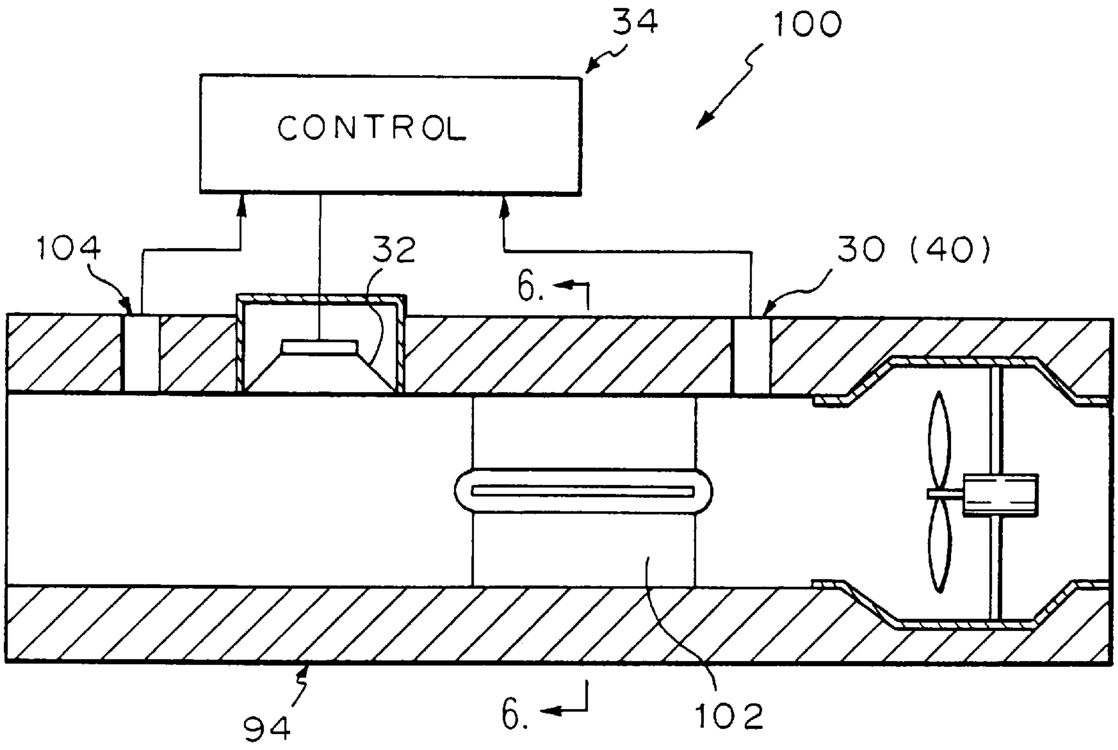
FIG. 5 is a cross-sectional view of a duct provided with a silencer in accordance with the third embodiment of this invention.
Figure 6:
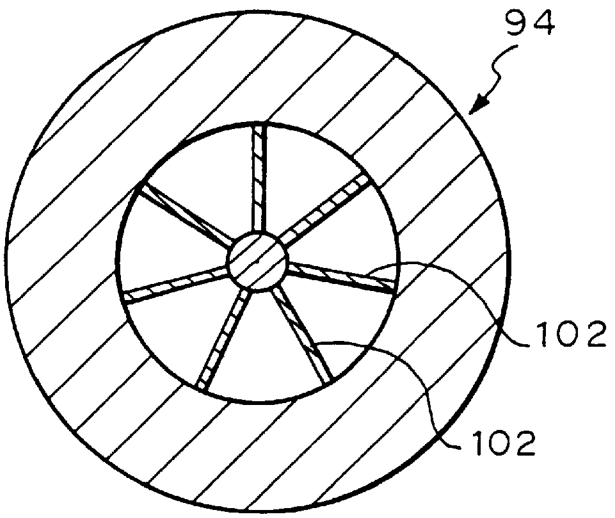
FIG. 6 is a view taken along the line 6—6 in FIG. 5.
Figure 7:
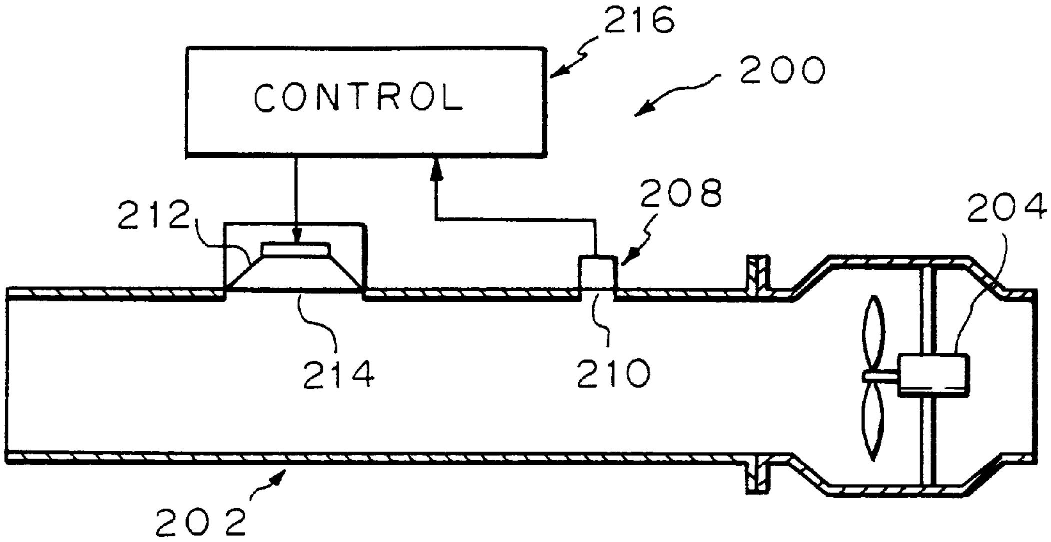
Fig. 7 (PRIOR ART)
FIG. 7 is a cross-sectional view of a duct provided with a prior art silencer.
Figure 8:
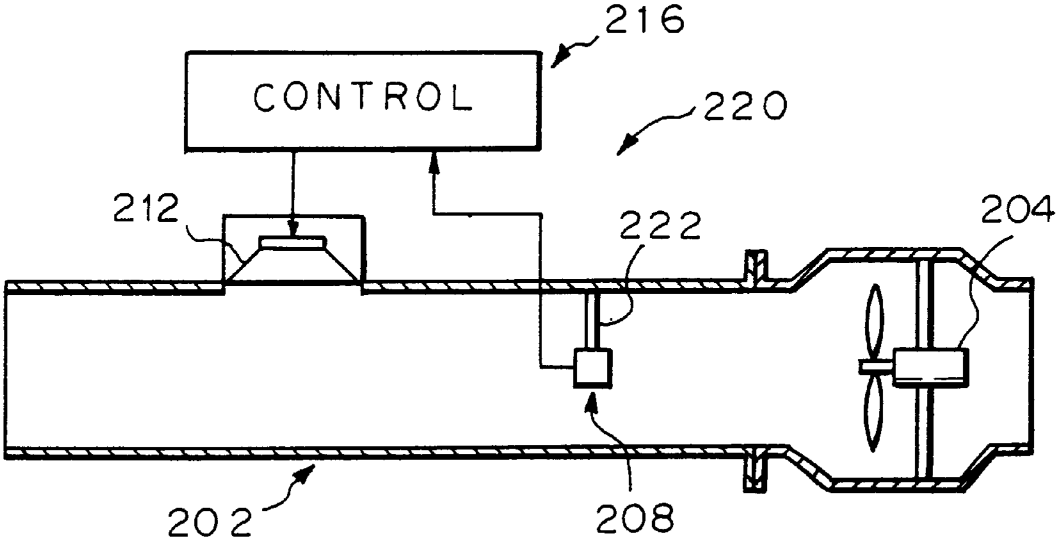
Fig. 8 (PRIOR ART)
FIG. 8 is a cross-sectional view of a duct provided with another prior art silencer.
Figure 9:
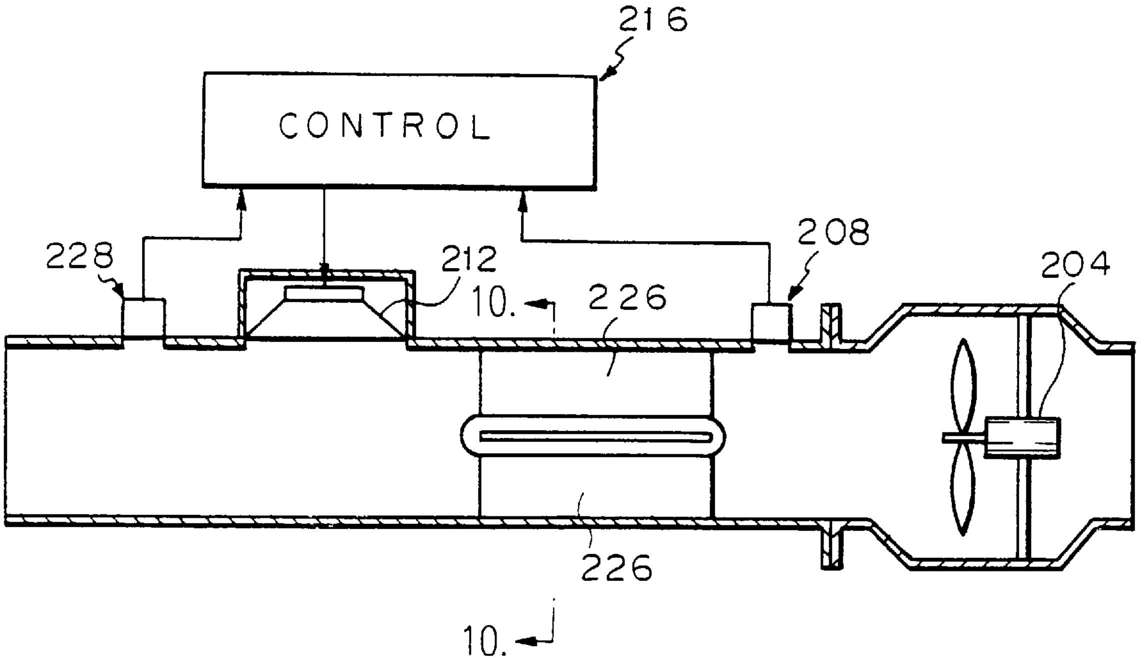
FIG. 9 is a cross-sectional view of a duct provided with the other prior art silencer; and, FIG. 10 is a view taken along the line 10—10 in FIG. 9.
Figure 10:
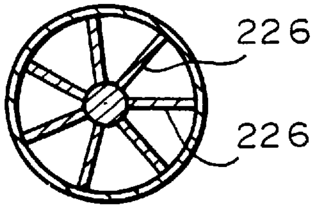

FIGS. 5 and 6 show a silencer 100 in accordance with the third embodiment which is generally the same as that of the second embodiment except for the fact that the former includes a plurality of rectangular sound absorption blades or partitions 102 and an error detecting microphone 104. For the sake of simplicity, the silencer is depicted with abbreviations of some elements and the same reference numerals are used for the same elements as in the preceding embodiments. The blades 102 are made from a sound absorption material such as glass wool in order to absorb the noise transmitted through the air passage segments defined by those blades. The error detecting microphone 104 detects any noise still remaining after the noise attenuation by the superimposition of the sound on the noise as stated above and delivers an error signal to the control.

Although this invention has been explained with reference with the drawings, the entire disclosure of Japanese Patent Application Nos. 8-257437 and 8-257438 filed on Sep. 5, 1996 including specifications, claims, drawings and summaries are incorporated herein by reference to their entirety.

What is claimed is:

1. A silencer mounted on an air duct for attenuating a sound or noise transmitted through the air passage of the duct, comprising:

a noise detecting microphone mounted on said duct for detecting said noise;

a loud speaker mounted on said duct to deliver, on the basis of the noise detected by said microphone into said air passage, a sound which is substantially the same as said noise except that the phase of the sound is the reverse of that of the noise to thereby enable the sound to be superimposed on the noise to thereby attenuate the noise; and vibration shield provided between said microphone with a windscreen and the wall of said duct for shielding any vibrations to be transmitted through said wall to said microphone so that said microphone detects said noise without any noise interference caused by said vibrations.

2. A silencer as set forth in claim 1 wherein:

said vibration shield includes a duct element made from a vibration damping or sound absorbing material and adapted to be incorporated into said duct to form a part of the same; and said noise detecting microphone is mounted on said duct element.

3. A silencer as set forth in claim 2 wherein:

said duct element is provided with a through hole radially extending therethrough;

said microphone is provided with said windscreen made from an open cell type porous elastomer around the noise or sound collecting portion of the microphone; and said windscreen is securely inserted into said through hole to thereby mount said microphone on the duct element.

4. A silencer as set forth in claim 3 wherein:

said windscreen inserted into said through hole has a radially inner surface which is substantially flush with the inner surface of said duct element and a radially outer surface provided with a recess therein;

said microphone is mounted on said radially outer surface of said windscreen in such a manner that said noise or sound collecting portion is inserted into said recess without any contact with the inner surface of said recess.

5. A silencer as set forth in claim 4 wherein:

said microphone has a fastening member connected thereto and securely inserted into said recess to thereby fasten said microphone on said windscreen;

a cushion member is provided between and engaged with said radially outer surface of said windscreen and said microphone; and said cushion member adds mass to the vibration system including said microphone and said windscreen, whereby said microphone is made to be less sensitive to high frequency vibration transmitted to said microphone through said windscreen.

6. A silencer as set forth in claim 4 further including a solid cover member covering said radially outer surface of said windscreen and said microphone mounted on said radially outer surface of said windscreen with a space left therebetween and sealingly connected to the outer surface of said duct element outside of said through hole provided in the duct element.

7. A silencer as set forth in claim 6 wherein:

said silencer further includes an error detecting microphone for detecting any noise still remaining after said noise attenuation by said superimposition of the sound on the noise; and said noise detecting microphone, said loud speaker and said error detecting microphone are positioned downstream of a source of said noise in the noise transmission direction in that order and spaced away from each other.

8. A silencer as set forth in claim 1 wherein:

said vibration shield includes a duct element adapted to be incorporated into said duct to form a part of the same and having a duct element body or duct element wall body made from a vibration damping or sound absorbing material and a rigid solid cover laid over the radially outer surface of said duct element body;

said duct element body includes a through hole radially extending therethrough;

said rigid solid cover includes an opening aligned with said through hole of said duct element body and having a diameter larger than that of said through hole;

said microphone is provided with said windscreen made from open cell type porous elastomer around the noise or sound collecting portion of the microphone; and said windscreen is securely inserted into said through hole of said duct element body to thereby mount said microphone on the duct element.

9. A silencer as set forth in claim 8 wherein:

said windscreen inserted into said through hole of said duct element body has a radially inner surface which is substantially flush with the inner surface of said duct element body and a radially outer surface provided with a recess therein;

said microphone is mounted on said radially outer surface of said windscreen in such a manner that said noise or sound collecting portion is inserted into said recess without any contact with the inner surface of said recess.

10. A silencer as set forth in claim 9 wherein:

said microphone has a fastening member connected thereto and securely inserted into said recess to thereby fasten said microphone on said windscreen;

a cushion member is provided between and engaged with said radially outer surface of said windscreen and said microphone; and said cushion member adds mass to the vibration system including said microphone and said windscreen, whereby said microphone is made to be less sensitive to high frequency vibration transmitted to said microphone through said windscreen.

11. A silencer as set forth in claim 9 further including a solid cover member covering said radially outer surface of said windscreen and said microphone mounted on said radially outer surface of said windscreen with a space left therebetween and sealingly connected to the outer surface of said rigid solid cover outside of said opening provided in the cover.

12. A silencer as set forth in claim 8 wherein:

said duct element further includes a sound permeable liner provided over the radially inner surface of said duct element body.

13. A silencer as set forth in claim 2, further comprising:

an error detecting microphone for detecting any noise still remaining after said noise attenuation by said superimposition of the sound on the noise;

said noise detecting microphone, said loud speaker and said error detecting microphone being mounted in said duct element downstream of a source of said noise in the noise transmission direction in that order and spaced away from each other so that the duct element enables the error detecting microphone not to be influenced by vibrations transmitted through the air duct.

14. A silencer as set forth in claim 2 further including partition walls provided in said duct element in such a manner that the walls radially extend from the central axis of the air passage of the duct element to the inner wall of said duct element to divide the air passage into a plurality of air passage segments extending in parallel with said center axis, said partition walls being made from a vibration damping or sound absorption material.

15. A silencer as set forth in claim 13 further including partition walls provided in said duct element in such a manner that the walls radially extend from the central axis of the air passage of the duct element to the inner wall of said duct element to divide the air passage into a plurality of air passage segments extending in parallel with said center axis, said partition walls being made from a vibration damping or sound absorption material.

16. A silencer as set forth in claim 1 wherein said vibration shield includes:

a vibration shield member made from a vibration damping or sound absorption material mounted on the outside of said duct where an opening is provided in the wall of the duct, the vibration shield member having a through hole extending radially relative to said duct; and said windscreen made from an open cell type porous elastomer installed into said through hole, the radially inner surfaces of the windscreen and said vibration shield member being substantially flush with the inner surface of said duct;

said windscreen having a recess formed in the radially outer surface of the windscreen, said noise detecting microphone being mounted on said windscreen in such a manner that the noise collecting portion of the microphone is positioned in said recess without any contact with the inner surface of said recess.

17. A silencer as set forth in claim 16 wherein:

said microphone has a fastening member connected thereto and securely inserted into said recess to thereby fasten said microphone on said windscreen;

a cushion member is provided between and engaged with said radially outer surface of said windscreen; and said cushion member adds mass to the vibration system including said microphone and said windscreen, whereby said microphone is made to be less sensitive to high frequency vibration transmitted to said microphone through said windscreen.

18. A silencer as set forth in claim 16 wherein said silencer further includes:

a first cover member covering the outer surface of said vibration shield member and sealingly connected to the outer surface of said duct, the cover member having an opening whereby the radially outer surface of said windscreen provided in said through hole of said noise shield member is exposed and said cover member does not engage with any portion of said radially outer surface of said windscreen; and a second cover member sealingly connected to the radially outer surface of said first cover member outside of said opening of said first cover member and covering said microphone on said windscreen without any contact with the same.

19. A silencer as set forth in claim 17 wherein said silencer further includes:

a first cover member covering the outer surface of said vibration shield member and sealingly connected to the outer surface of said duct element, the cover member having an opening whereby the radially outer surface of said windscreen provided in said through hole of said noise shield member is exposed and said cover member does not engage with any portion of said radially outer surface of said windscreen provided in said through hole of said noise shield member; and a second cover member sealingly connected to the radially outer surface of said first cover member outside of said opening and covering said microphone on said windscreen without any contact with the same.

20. A silencer as set forth in claim 1, wherein said microphone includes a windscreen positioned between said microphone and said duct.

* * * * *